(12) United States Patent
Jayaraman et al.

(10) Patent No.: US 12,024,561 B2
(45) Date of Patent: *Jul. 2, 2024

(54) STABLE ANTIBODY FORMULATION

(71) Applicant: DR. REDDY'S LABORATORIES LIMITED, Hyderabad (IN)

(72) Inventors: Murali Jayaraman, Kancheepuram (IN); Anuja Chandrasekar, Chennai (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 277 days.

This patent is subject to a terminal disclaimer.

(21) Appl. No.: 17/045,336

(22) PCT Filed: Apr. 10, 2019

(86) PCT No.: PCT/IN2019/050291
§ 371 (c)(1),
(2) Date: Oct. 5, 2020

(87) PCT Pub. No.: WO2019/198099
PCT Pub. Date: Oct. 17, 2019

(65) Prior Publication Data
US 2021/0253714 A1   Aug. 19, 2021

(30) Foreign Application Priority Data
Apr. 10, 2018   (IN) .............................. 201841013645

(51) Int. Cl.
*C07K 16/28* (2006.01)
*A61K 39/00* (2006.01)
*A61K 47/26* (2006.01)

(52) U.S. Cl.
CPC .......... *C07K 16/2839* (2013.01); *A61K 47/26* (2013.01); *A61K 2039/505* (2013.01); *C07K 2317/24* (2013.01); *C07K 2317/94* (2013.01)

(58) Field of Classification Search
CPC ............ C07K 16/2839; C07K 2317/24; C07K 2317/94; A61K 47/26; A61K 2039/505
See application file for complete search history.

(56) References Cited

U.S. PATENT DOCUMENTS

2010/0098712 A1* 4/2010 Adler .................. A61K 9/0019
424/172.1
2014/0341885 A1* 11/2014 Diluzio ..................... A61P 1/18
424/133.1

FOREIGN PATENT DOCUMENTS

WO      2010/102241 A1    9/2010
WO      WO-2020252069 A1 * 12/2020    ....... A61K 39/39591
WO      WO-2020252072 A1 * 12/2020    ................ A61P 1/04

OTHER PUBLICATIONS

International Search Report dated Jul. 18, 2019, for corresponding International Patent Application No. PCT/IN2019/050291.
Written Opinion dated Jul. 18, 2019, for corresponding International Patent Application No. PCT/IN2019/050291.

* cited by examiner

*Primary Examiner* — Gregory S Emch
*Assistant Examiner* — Ashley H. Gao
(74) *Attorney, Agent, or Firm* — Pergament & Cepeda LLP; Milagros A. Cepeda; Edward D. Pergament

(57) ABSTRACT

The present invention discloses a stable pharmaceutical formulation of an antibody, wherein the formulation contains buffer, surfactant and salt, and wherein the formulation is devoid of free amino acids. The disclosed antibody formulations are liquid formulations that are also suitable for lyophilization.

7 Claims, 1 Drawing Sheet

STABLE ANTIBODY FORMULATION

This application is a National Stage Application under 35 U.S.C. § 371 of PCT International Application No. PCT/IN2019/050291, filed Apr. 10, 2019, which claims the benefit of Indian provisional patent application No. 201841013645 filed on Apr. 10, 2018, all of which are herein incorporated by reference in their entireties.

FIELD OF INVENTION

The present invention is related to stable formulations of an antibody molecule, wherein the antibody is stabilized with minimal excipients. The disclosed formulations are compatible with lyophilized as well as liquid form and also suitable for intravenous and/or subcutaneous route of administration.

BACKGROUND

Over the past two decades, recombinant DNA technology has led to the commercialization of many proteins, particularly antibody therapeutics. The effectiveness of these therapeutic antibodies is majorly dependent on the stability, route of administration and their dosage forms and concentrations. This in turn, necessitates therapeutic antibodies to be formulated appropriately to retain the stability and activity of a therapeutic antibody.

Formulations for each route of administration and dosage forms may be unique and, therefore, have specific requirements. Solid dosage forms, such as lyophilized powders, are generally more stable than liquid (aqueous) formulations. However, reconstitution of the lyophilized formulation requires a significant vial overfill, care in handling and involves high production cost relative to a liquid formulation. While liquid formulations are advantageous in these and are usually preferred for injectable protein therapeutics (in terms of convenience for the end user and ease of preparation for the manufacturer), this form may not always be feasible given the susceptibility of proteins to denaturation, aggregation and oxidation under stresses such as temperature, pH changes, agitation etc. All of these stress factors could result in the loss of biological activity of a therapeutic protein/antibody. In particular, high concentration liquid formulations are susceptible to degradation and/or aggregation. Nevertheless, high concentration formulations may be desirable for subcutaneous or intravenous route of administration, as the frequency of administration and injection volume is reduced. On the other hand, specific treatment schedule and dosing might require a low concentration formulation and prefer intravenous route of administration for more predictable delivery and complete bioavailability of the therapeutic drug.

Hence, designing a formulation that is stable at high or low concentrations of the therapeutic protein/antibody, aiding in different route of administration (intravenous or subcutaneous) and which is suitable in lyophilized or liquid form, pose a significant developmental challenge. Further, every protein or antibody with its unique characteristics and properties of degradation, adds to the complexity in the development of a stable formulation and may demand a specific formulation.

A stable formulation of a therapeutic protein or antibody involves addition of a wide variety of stabilizers/excipients including amino acids, sugars, polyols, surfactants, salts, polymers, amines, anti-oxidants, chelators etc. Many of the FDA approved therapeutic proteins/antibodies contain more than one category of stabilizers.

A formulation combination with increased concentration of protein and/or stabilizers may increase the viscosity of the formulation, in turn increasing the injection time and pain at the site of injection and also pose difficulties during processing of the drug substance. Hence, it is necessary to develop an improved formulation, in lyophilized as well as liquid form which contains minimal number or concentration of excipients, yet stabilizing the drug at a wide range of its concentration.

SUMMARY

The present invention discloses a stable pharmaceutical formulation of an antibody comprising buffer, salt and surfactant, wherein the said formulation is devoid of free amino acid. The disclosed formulation optionally contains sugar/s.

In particular, the invention discloses a stable pharmaceutical formulation of α4β7 antibody comprising buffer, sugar, salt and surfactant wherein the said formulation is devoid of free amino acids. The antibody in the said formulation is stable for four weeks at 40° C. and maintains at least 95% of monomeric content of the antibody in the formulation. The antibody is also stable at 50° C. for two weeks and maintains at least 97% of monomeric content of the antibody in formulation.

Salt present in the disclosed α4β7 antibody formulation controls the rate of fragmentation of antibody molecule, as well as the rate of conversion of main peak content to basic variant, and stabilizes the formulation.

BRIEF DESCRIPTION OF DRAWINGS

FIG. 1(a) represents LMW content,

FIG. 1(b) represents monomer content during storage conditions at 40° C. for four weeks.

DETAILED DESCRIPTION OF THE INVENTION

Definitions

Figure 1:
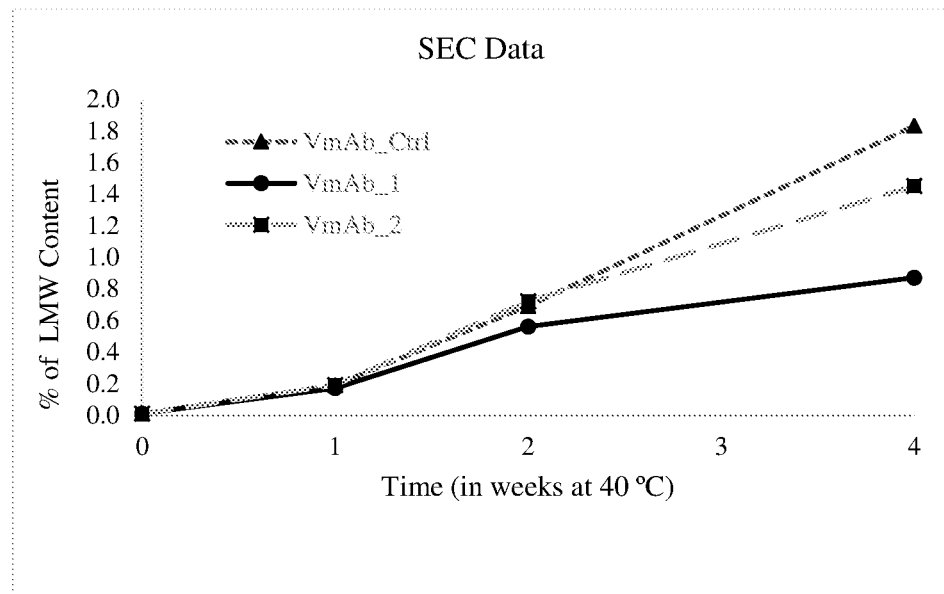
FIG. 1 illustrates the effect of salt on the LMW and monomer content of vedolizumab (60 mg/ml) formulations prepared as per example 1 and analyzed using SEC chromatography.
Figure 1:
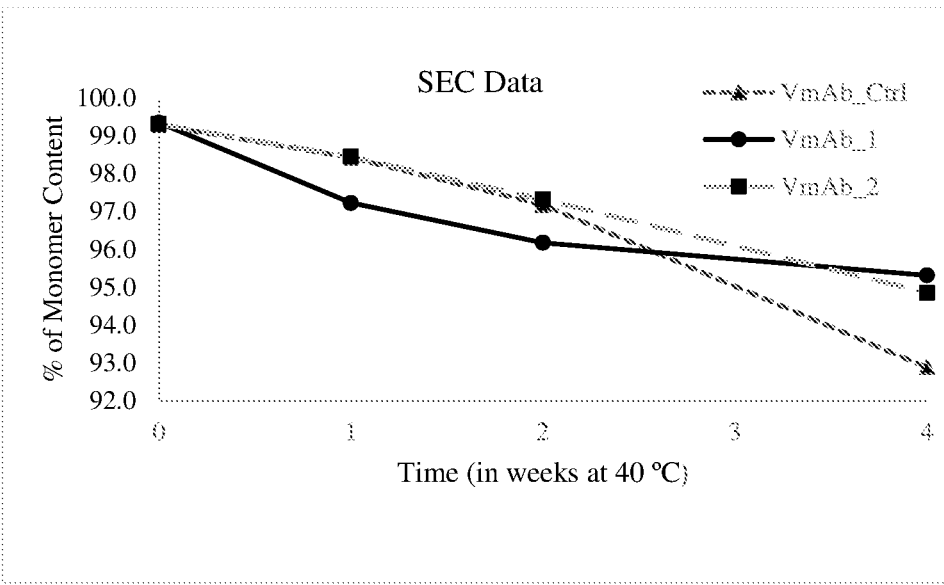

The term "antibody" refers to a glycoprotein comprising at least two heavy (H) chains and two light (L) chains inter-connected by disulfide bonds, or an antigen-binding portion thereof. The "antibody" as used herein encompasses whole antibodies or any antigen binding fragment (i.e., "antigen-binding portion") or fusion protein thereof.

The term "stable" formulation refers to the formulation wherein the antibody therein retains its physical stability and/or chemical stability and/or biological activity upon storage.

Stability studies provides evidence of the quality of an antibody under the influence of various environmental factors during the course of time. ICH's "Q1A: Stability Testing of New Drug Substances and Products," states that data from accelerated stability studies can be used to evaluate the effect of short-term excursions higher or lower than label storage conditions that may occur during the shipping of the antibodies.

Various analytical methods are available for measuring the physical and chemical degradation of the antibody in the pharmaceutical formulations. An antibody "retains its physical stability" in a pharmaceutical formulation if it shows substantially no signs of aggregation, precipitation and/or denaturation upon visual examination of color and/or clarity, or as measured by UV light scattering or by size exclusion chromatography. An antibody is said to "retain its chemical stability" in a pharmaceutical formulation when its shows no or minimal formation of product variants which may include variants as a result of chemical modification of antibody of interest such as deamination, oxidation etc. Analytical methods such as ion exchange chromatography and hydrophobic ion chromatography may be used to investigate the chemical product variants.

The term 'monomer' as used herein describes antibodies consisting of two light chains and two heavy chains. The monomer content of an antibody composition is typically analyzed by size exclusion chromatography (SEC). As per the separation principle of SEC the large molecules or molecules with high molecular weight (HMW) elute first followed by smaller or lower weight molecules. In a typical SEC profile for an antibody composition, aggregates that may include dimers, multimers, etc., elute first, followed by the monomer, and the clipped antibody variants or degradants may be eluted last. In some circumstances the aggregate peak or the degradant peaks may not elute as a baseline separated peaks but instead as a shoulder or abnormal broad peaks. In order to maintain the appropriate activity of an antibody, in particular of a therapeutic antibody, it is desirable to reduce the formation of aggregate or fragmentation of products and hence control the monomer content to a target value. Ability to inhibit the formation of aggregate and degradant content as measured at various time points during stability studies may indicate the suitability of the candidate formulation for antibody of interest. TSKgel® G3000SWXL (7.8 mm×30 cm) column from Tosoh Bioscience LLC can be used on water HPLC to perform SEC.

Pharmaceutically acceptable excipients refer to the additives or carriers, which may contribute to stability of the antibody in formulation. The excipients may encompass stabilizers and tonicity modifiers. Examples of stabilizers and tonicity modifiers include, but not limited to, sugars, polyols, salts, surfactants, and derivatives and combination thereof.

Sugar/s herein includes sugars and sugar alcohols such as polyols. Sugars can be referred to monosaccharides, disaccharides, and polysaccharides. Examples of sugars include, but are not limited to, sucrose, trehalose, glucose, dextrose, raffinose and others. Examples of polyols include, but are not limited to, mannitol, sorbitol, and others.

Surfactant refers to pharmaceutically acceptable excipients used to protect the protein formulations against various stress conditions, like agitation, shearing, exposure to high temperature etc. The suitable surfactants include but are not limited to polyoxyethylenesorbitan fatty acid esters such as Tween 20™ or Tween 80™, polyoxyethylene-polyoxypropylene copolymer (e.g. Poloxamer, Pluronic), sodium dodecyl sulphate (SDS) and the like or combination thereof.

The term "free amino acid" as used herein refers to amino acid that is included in the formulation and is not a part of the buffer component. An amino acid may be present in its D- and/or L-form. The amino acid may be present as any suitable salt e.g. a hydrochloride salt, such as Arginine-HCl.

Examples of salts include, but not limited to, sodium chloride, potassium chloride, magnesium chloride, sodium thiocyanate, ammonium thiocyanate, ammonium sulfate, ammonium chloride, calcium chloride, zinc chloride and/or sodium acetate.

Certain specific aspects and embodiments of the invention are more fully described by reference to the following examples. However, these examples should not be construed as limiting the scope of the invention in any manner.

DETAILED DESCRIPTION OF THE EMBODIMENTS

The present invention discloses a stable pharmaceutical formulation of an antibody comprising buffer, salt and surfactant.

In one embodiment, the invention discloses a stable pharmaceutical formulation of an antibody comprising buffer, salt and surfactant, wherein the formulation does not contain free amino acid.

In the above embodiment of the invention, the salt present in the antibody formulation is sodium chloride and it controls rate of fragmentation of the antibody molecule in the formulation at a concentration from 10 mM to less than about 100 mM. Preferably the salt concentration is from 20 mM to 90 mM.

In the above said embodiment, the salt present in the formulation controls the rate of conversion of main peak content to basic variants and in addition reduces fragmentation of the antibody molecule, during storage.

In the above embodiment, the antibody is a therapeutic monoclonal antibody and is selected from the group consisting of chimeric antibody, humanized antibody and human antibody.

In the above mentioned embodiment, the therapeutic antibody is a humanized antibody and binds to α4β7.

In an embodiment, the invention discloses a stable α4β7 antibody formulation comprising buffer, salt and surfactant, wherein the formulation does not contain free amino acid.

In the above said embodiment, the α4β7 antibody formulation is stable and maintains at least 95% of monomeric content of the antibody, when stored at 40° C. for four weeks.

In the above said embodiment, the α4β7 antibody formulation is stable and contains less than 1% of low molecular weight (LMW) species or fragments in the formulation, when stored at 40° C. for four weeks.

In any of the above said embodiments of the invention, α4β7 antibody formulation optionally contains sugar/s. Preferably, the sugar is sucrose or trehalose.

In any of the above said embodiments, the buffer mentioned in the formulation includes organic buffer, inorganic buffer and/or combinations thereof.

In the above mentioned embodiment of the invention, the said organic buffer includes histidine buffer, succinate buffer or acetate buffer.

In yet another embodiment of the invention, the inorganic buffer mentioned in the formulation includes phosphate buffer.

In all of the above mentioned embodiments of the invention, the concentration of the antibody in the formulation is about 50 mg/ml to about 200 mg/ml.

In any of the above mentioned embodiments of the invention, the pH of α4β7 antibody formulation is from 6.0-7.0.

In one embodiment, the invention discloses a stable pharmaceutical formulation of α4β7 antibody comprising buffer, sodium chloride, surfactant, and sugar, wherein the formulation does not contain a free amino acid.

In the above said embodiment, the α4β7 antibody formulation is stable and maintains at least 97% of monomeric content of the antibody and controls the low molecular weight species to less than 1.5% in the formulation, when stored at 50° C. for two weeks.

In an embodiment, the α4β7 antibody formulation comprising buffer, sodium chloride, surfactant and sugar, contains less than 15% of basic variants, and less than about 1.5% of low molecular weight species when stored at 50° C. for two weeks.

In any of the above mentioned embodiments of the invention, the salt present in the α4β7 antibody formulation is at a concentration selected from the range, 10 mM to less than about 100 mM, preferably 20 mM to 90 mM.

In any of the above mentioned embodiments of the invention, the salt can be sodium chloride, potassium chloride, ammonium chloride or ammonium sulphate.

In any of the above embodiments, salt present in the formulation helps in maintaining main peak content and also controls the rate of conversion of main peak content to basic variants and in addition reduces fragmentation of the antibody molecule during storage. Storage conditions herein includes accelerated stability and shelf stability conditions.

In any of the above mentioned embodiments, the formulation of α4β7 antibody is a stable liquid (aqueous) formulation, which can be used for parenteral administration. Parenteral administration includes intravenous, subcutaneous, intra peritoneal, intramuscular administration or any other route of delivery generally considered to be falling under the scope of parenteral administration and as is well known to a skilled person.

In any of the above embodiments of the invention, the stable liquid/aqueous formulation is suitable and can be lyophilized as lyophilized powders. Further, the lyophilized formulation of α4β7 antibody can be reconstituted with appropriate diluent to achieve the liquid formulation suitable for administration.

The disclosed formulations of the invention uses lesser amounts of excipients to stabilize the therapeutic antibody.

EXAMPLES

An α4β7 antibody, vedolizumab, suitable for storage in the present pharmaceutical composition is produced by standard methods known in the art. For example, vedolizumab is prepared by recombinant expression of immunoglobulin light and heavy chain genes in a mammalian host cell such as Chinese Hamster Ovary cells. Further, the expressed vedolizumab is harvested and the crude harvest is subjected to standard downstream process steps that include purification, filtration and optionally dilution or concentration steps. For example, the crude harvest of vedolizumab may be purified using standard chromatography techniques such as affinity chromatography, ion-exchange chromatography and combinations thereof. The purified vedolizumab solution can additionally be subjected to one or more filtration steps, and the solution obtained is subjected to further formulation studies.

Example 1: Formulation of Vedolizumab without Sugars and Free Amino Acids

To achieve a stable formulation of vedolizumab without free amino acid and sugars, as part of experimental design, different concentrations of sodium chloride solution was prepared. Vedolizumab (at a concentration of 7 mg/ml) in Tris acetate buffer obtained from downstream chromatographic process was buffer exchanged and concentrated in 50 mM histidine buffer up to 65 mg/ml of concentration of the antibody. The concentrated antibody was divided into three samples. 50 mM and 100 mM sodium chloride was added to two samples of vedolizumab. 0.6 mg/ml polysorbate 80 was added to all three vedolizumab samples. The sample which does not contain sodium chloride was used as control in this experiment. Details of all the three vedolizumab formulations are mentioned in Table 1. All vedolizumab formulations were subjected for accelerated stability studies at 40° C. for four weeks. Post which, the samples were analyzed for low molecular weight (LMW) species and monomer content [results are shown in FIGS. 1(a) and 1(b)] using size exclusion chromatography (SEC) and also checked for visual inspection [Table 2].

TABLE 1

Compositions of various vedolizumab formulations without sugars and free amino acid

| Sample Name | Composition |
| --- | --- |
| Vmab-Control | Vedolizumab 60 mg/ml, 50 mM histidine monohydrochloride, 0.6 mg/mL polysorbate 80 |
| Vmab-1 | Vedolizumab 60 mg/ml, 50 mM histidine monohydrochloride, 50 mM NaCl, 0.6 mg/mL polysorbate 80 |
| Vmab-2 | Vedolizumab 60 mg/ml, 50 mM histidine monohydrochloride, 100 mM NaCl, 0.6 mg/mL polysorbate 80 |

TABLE 2

Visual inspection data of vedolizumab (60 mg/ml) formulations prepared as per example 1

| | Visual Inspection at 40° C. | | | |
| --- | --- | --- | --- | --- |
| Sample Name | 0 W | 1 W | 2 W | 4 W |
| Vmab-Control | Clear | Opalescent | opalescent | Turbid |
| Vmab-1 | Clear | Clear | Clear | Slightly turbid |
| Vmab-2 | Clear | opalescent | opalescent | opalescent |

W—indicates weeks

Example 2: Formulations of Vedolizumab without Free Amino Acids

To achieve a stable formulation of vedolizumab with sugar and without free amino acids, as part of experimental design, vedolizumab 60 mg/ml is formulated in following buffer composition containing 20 mM phosphate buffer, 50 mM sodium chloride, 60 mg/ml sucrose and 0.6 mg/ml polysorbate 80. The concentration of sodium chloride was selected from the above experiment which gave more stability to the antibody. Vedolizumab formulations, without sodium chloride, were used as control/s in this experiment. Details of the formulation used in this experiment is given in Table 3. The samples were subjected for accelerated stability studies at 50° C. for two weeks. Post which, the samples were analyzed for low molecular weight (LMW) species and monomer content [results are shown in Table -4] using size exclusion chromatography (SEC) and main peak content, acidic, basic variants using ion-exchange chromatography [Table 5] and also checked for visual inspection [Table 7].

TABLE 3

Compositions of various vedolizumab formulations without free amino acid

| Sample Name | Composition |
|---|---|
| Vmab-S | Vedolizumab 60 mg/ml, 20 mM phosphate buffer, 0.6 mg/mL polysorbate 80, sucrose 60 mg/ml |
| Vmab-SA1 | Vedolizumab 60 mg/ml, 20 mM phosphate buffer, 0.6 mg/mL polysorbate 80, sucrose 60 mg/ml, 5.3 mg/ml of arginine |
| Vmab-SA2 | Vedolizumab 60 mg/ml, 20 mM phosphate buffer, 0.6 mg/mL polysorbate 80, sucrose 60 mg/ml, 10.6 mg/ml of arginine |
| Vmab-3 | Vedolizumab 60 mg/ml, 20 mM phosphate buffer, 50 mM sodium chloride, 0.6 mg/mL polysorbate 80, sucrose 60 mg/ml |

TABLE 4

SEC data of vedolizumab (60 mg/ml) formulations prepared as per example

| Sample Name | % of LMW at 50° C. | | | % of monomer at 50° C. | | |
|---|---|---|---|---|---|---|
| | 0 W | 1 W | 2 W | 0 W | 1 W | 2W |
| Vmab-S | 0.0 | 0.6 | 1.0 | 99.3 | 97.8 | 97.2 |
| Vmab-SA1 | 0.7 | 1.9 | 1.9 | 99.2 | 97.5 | 97.2 |
| Vmab-SA2 | 0.7 | 1.2 | 1.8 | 99.3 | 98.3 | 97.3 |
| Vmab-3 | 0.0 | 0.7 | 1.2 | 99.2 | 97.8 | 97.1 |

W-indicates weeks

TABLE 5

IEX data of vedolizumab (60 mg/ml) formulation prepared as per example 2

| Sample Name | Acidic content at 50° C. | | Main peak content at 50° C. | | Basic variants at 50° C. | |
|---|---|---|---|---|---|---|
| | 0 W | 2 W | 0 W | 2 W | 0 W | 2 W |
| Vmab-S | 15.8 | 43.3 | 75.0 | 39.1 | 9.2 | 17.1 |
| Vmab-SA1 | 15.9 | 40.7 | 74.7 | 36.2 | 9.4 | 22.4 |
| Vmab-SA2 | 18.1 | 46.2 | 75.0 | 38.9 | 6.8 | 14.0 |
| Vmab-3 | 19.7 | 45.8 | 72.0 | 39.2 | 8.4 | 14.6 |

W-indicates weeks

TABLE 6

Percentage of main peak content of vedolizumab formulations prepared as per example 2.

| Sample Name | % Main peak content at 50° C. | | % of main peak content retained at the end of 2 W |
|---|---|---|---|
| | 0 W | 2 W | |
| Vmab-S | 75.0 | 39.1 | 52.1 |
| Vmab-SA1 | 74.7 | 36.2 | 48.4 |
| Vmab-SA2 | 75.0 | 38.9 | 51.9 |
| Vmab-3 | 72.0 | 39.2 | 54.4 |

W-indicates weeks

TABLE 7

Visual inspection data of vedolizumab (60 mg/ml) formulation prepared as per example 2

| Sample Name | Visual Inspection at 50° C. | | |
|---|---|---|---|
| | 0 W | 1 W | 2 W |
| Vmab-S | Slightly Opalescent | Slightly Opalescent | Slightly Opalescent |
| Vmab-SA1 | Slightly Opalescent | Opalescent | Opalescent |
| Vmab-SA2 | Slightly Opalescent | Slightly Opalescent | Slightly Opalescent |
| Vmab-3 | Clear | Slightly opalescent | Slightly opalescent |

W-indicates weeks

Liquid Vedolizumab formulations prepared from example 1 and example 2 are suitable for lyophilization and subjected for the lyophilization process using techniques known in the art and checked for stability

The invention claimed is:

1. A pharmaceutical formulation of an α4β7 antibody, comprising 60 mg/ml of the α4β7 antibody, buffer, 20 mM to less than 100 mM sodium chloride, and 0.6 mg/ml polysorbate 80 surfactant and wherein the formulation is devoid of free amino acid and sugar.

2. The pharmaceutical formulation of an α4β7 antibody of claim 1, wherein the sodium chloride decreases the rate of fragmentation of the antibody molecule in the formulation.

3. The pharmaceutical formulation of an α4β7 antibody according to claim 1, is stable and maintains at least 95% of monomeric content of the antibody and controls the low molecular weight species to less than 1% in the formulation, when stored at 40° C. for four weeks.

4. The pharmaceutical formulation of an α4β7 antibody of claim 1, which has a pH of 6.0 to 7.0.

5. The pharmaceutical formulation of an α4β7 antibody of claim 1, which is a liquid or lyophilized formulation.

6. The pharmaceutical formulation of an α4β7 antibody of claim 1, wherein the α4β7 antibody is vedolizumab.

7. The pharmaceutical formulation of an α4β7 antibody of claim 1, wherein the sodium chloride is of 20 mM to 90 mM.

* * * * *